United States Patent [19]

Jimenez Collado et al.

[11] Patent Number: 5,968,497
[45] Date of Patent: *Oct. 19, 1999

[54] COMPOSITIONS CONTAINING DIALKYL ($C_1$-$C_6$)-KETONE PEROXIDE FOR THE PRESERVATION OF ANIMAL AND HUMAN DEAD TISSUES

[75] Inventors: Juan Jimenez Collado, Madrid, Spain; Edgar Arene Rada, Lapaz, Bolivia; Ramón Chavez Inzunza, Madrid, Spain

[73] Assignee: Universidad Complutense de Madrid, Madrid, Spain

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,403

[22] PCT Filed: Dec. 19, 1995

[86] PCT No.: PCT/ES95/00151

§ 371 Date: Feb. 18, 1997

§ 102(e) Date: Feb. 18, 1997

[87] PCT Pub. No.: WO96/28024

PCT Pub. Date: Sep. 19, 1996

[30] Foreign Application Priority Data

Mar. 9, 1995 [ES] Spain ................................. 9500471
Aug. 1, 1995 [ES] Spain ................................. 9501559

[51] Int. Cl.⁶ ....................................... A01N 1/00
[52] U.S. Cl. ............................... 424/75; 27/22.1; 27/22.2
[58] Field of Search ................... 424/75; 568/559; 27/1, 22.1, 22.2

[56] References Cited

U.S. PATENT DOCUMENTS 5,837,159 11/1998 Farkas et al. ........................... 252/193

FOREIGN PATENT DOCUMENTS 57040507 3/1982 Japan .
1072728 6/1967 United Kingdom .

OTHER PUBLICATIONS

Logani et al. Skin–Tumour Promoting Activity of Methyl Ethyl Ketone Peroxide—A Potent Lipid–Peroxidizing Agent. Food Chem. Toxicol. 22(11), pp. 879–882. (Nov. 1984). Abstract Only.

Ando et al. Methyl Ethyl Ketone Peroxide Damage to Cytochrome P–450 Peroxidase Activities. Toxicol.–Appl–Pharmacol. vol. 81, No. 3, Pt. 1, Dec. 1985. pp. 517–524. Abstract Only.

Spaulding et al. Chemically Induced Skin Carcinogenesis in a Transgenic Mouse Line (TG AC) Carrying a v–Ha–ras Gene. Carcinogenesis, 14(7), pp. 1335–1341. (Jul. 1993).

*Primary Examiner*—Robert H. Harrison
*Attorney, Agent, or Firm*—Klauber & Jackson

[57] ABSTRACT

The compositions for the preservation of organic tissues are comprised of a mixture from 12 to 70% of at least one dialkyl ($C_1$–$C_6$)-keton peroxide, from 10 to 15% of glycerine, from 10 to 70% of at least one alcohol and, optionally, from 0 to 10% of a complementary marking, coloring and/or aromatic agent. Said compositions may be mixed with other appropriate agents or diluents, and can be applied especially to the preservation of tissues of all types, of human or origin, preferably by embalming or immersion.

39 Claims, No Drawings

COMPOSITIONS CONTAINING DIALKYL ($C_1$-$C_6$)-KETONE PEROXIDE FOR THE PRESERVATION OF ANIMAL AND HUMAN DEAD TISSUES

This application is a 371 of PCT/ES95/00151, filed Nov. 19, 1995.

TECHNICAL FIELD OF THE INVENTION

The present invention fits in the technical field of the preservation of organic animal or human tissues. More specifically, the invention provides compositions useful for temporary or indefinite preservation of dead tissues and human and animal corpses, against natural rotting processes and contamination with fungi.

PRIOR ART OF THE INVENTION

Preservation of animal and human corpses as well as of organs and tissues removed from said corpses has a long tradition in history initially due to cultural reasons and, approximately since the Renaissance also for the purpose of anatomical studies.

Nowadays, the preservation of human corpses is still done for cultural reasons but also for pathological and anatomical studies and the transport of corpses from one place to another. Likewise, the preservation of animal corpses is still being used, in public and private education, in addition to the above mentioned purposes.

Current preservation technologies are essentially based on embalming techniques and by immersion for which different agents are used. Such agents are alcohol as a fixing agent and preservative, tannic acid as a means to prevent the growth of fungi, mercury bichloride to inhibit decay and to facilitate mummification, arsenic, glycerol, paraffin, combinations of acetone and silicone as well as formaldehyde or formol discovered by the chemist Wilhelm V, Hofmann in 1868. Due to its low cost and excellent preserving properties, formol is still the agent most widely used as the preservative of animal and human corpses and tissues and its cost is still low.

However, due to its relative toxicity and its possible harmful and even cancerigenic effects, the use of formaldehyde is presently being questioned in scientific circles and by health administrations and there are studies and projects that consider the prohibition of the use of formol as a preservative. Aside from this, formaldehyde also has the well known disadvantages such as being an agent that irritates the mucous membranes and respiratory tract and that also has a typical smell that is usually perceived as very unpleasant.

On the other hand, by means of conventional preservation techniques and the use of current preservatives, total protection of the tissues against natural processes of decay by microbiological agents, fungi is not achieved, nor is the restoration of said tissues in a flexible state as similar as the state of live tissues.

Conventional temporary preservation techniques, necessary or convenient in some cases for example in the case of the transport of corpses, preservation in funeral homes before burial or in forensic institutions before an autopsy is carried out, are essentially limited to placement of corpses in refrigerating vaults, or arterial insufflation or insufflation of body cavities with formol, which does not produce a satisfactory preservation, aside from the fact that, in the cases of vaults, there are high construction, operation and maintenance costs of the refrigerating vaults. And in the case of arterial insufflation, a highly specialized technician is required.

On the other hand, in practice techniques are carried out for the preparation of anatomical samples in which formaldehyde/formol are used. Said techniques are the whitening of bones, restoration of corpses, bodies of mummified animals and parts of the same, staining of nervous tissue, flexibilization of hollow viscera, obtainment of samples of blood vessels by corrosion-reflection techniques, as well as the diaphanization of animal bodies or fetuses.

With the conventional bone whitening techniques, carried out with aggressive detergents, the result does not tend to be totally satisfactory in view of the fact that it is difficult to obtain uniform whitening, besides the fact that the aggressiveness of the detergents used damages the texture of the treated bone.

With the conventional techniques of restoration of animal or human corpses or parts thereof, up to now, a technique that allows flexibilization of the mummified tissues, as well as a preservation that allows exposure thereto to room temperature and easy maintenance of the preservation effects, has not been achieved.

With the conventional staining techniques of pieces of nervous tissue of the central nervous system and of flexibilization/preservation of hollow viscera, the obtainment of samples of blood vessels by corrosion-reflection techniques, as well as the diaphanization of animal bodies or fetuses, it is practically impossible to achieve anatomical pieces that are preserved with a high degree of flexibility and that exposed without protection, are preserved with decaying.

On the other hand, with the conventional corrosion/reflection techniques, it is very difficult if not to say practically impossible, to obtain the maintenance of most of the finer capillaries, while a subsequent big disadvantage of the conventional diaphanization techniques is the long processing time (about 120) that they tend to require.

Subsequent research carried out on the basis of that which has been described in Spanish patent P-9500471 has resulted in that the compositions with the basic components described therein may be used in other useful applications, such as the temporary preservation of corpses by means of spraying/nebulization or smearing, whitening of bones, restoration of corpses, mummified animal bodies and pieces of the same, staining of nervous tissue, flexibilization of hollow viscera, obtainment of samples of blood vessels by corrosion-reflection techniques, as well as the diaphanization of animal bodies or fetuses.

The present invention has the purpose of overcoming the inconveniences of the prior art by means of a product with negligible toxicity that is easy to prepare and handle, practically odorless and rapidly acting and with a low cost, that makes it possible to preserve and restore, in a very flexible state very similar to the live structure and texture, all types of animal tissues, whether they are whole bodies or parts of bodies or tissues removed from them.

Additionally, due to its antithrombotic and thrombolitic characteristics, the product permits injection thereof into tissues and corpses through the blood vessels without any previous preparation, that is to say, without previous washing of the blood vessels, without the use of compressors, antithrombotic substances, etc.

DETAILED DESCRIPTION OF THE INVENTION

The present invention, just as its title indicates and as defined in the claims, refers to compositions that contain dialkyl ($C_1$–$C_6$) ketone peroxide preferably ethyl-methyl ketone peroxides and methyl-isobutyl ketone peroxides or mixtures thereof for the preservation of organic tissues as well as the use of said compositions in the preservation and partial regeneration of animal or human organic tissues. Likewise, the compositions are useful in the preparation of anatomical pieces.

The compositions are characterized generally in that they comprise a mixture (in volume %) of:

12 to 70% of at least one dialkyl ($C_1$–$C_6$) ketone peroxide;

10 to 15% glycerol;

15 to 75% of at least one alcohol and;

from 0 to 10% of a marker, stain and/or aromatizing agent.

The presence of markers, stains or aromatizing agents, such as sarsaparilla, chloral hyrate, citronella, etc., is optional.

The compositions serve for conventional preservation techniques by arterial insufflation or embalming, as well as by immersion and combinations of both techniques.

Likewise, a technique of surface application by smearing or nebulization/spraying, that will be described hereinafter, may be used for temporary preservation.

For preservation techniques by arterial insufflation (embalming) of human and mammal corpses and tissues for an indefinitely long period of time, the compositions preferably have the following formulation:

50–70% dialkyl ($C_1$–$C_6$) ketone peroxide;

10–15% glycerol;

15–30% alcohol;

0–5% of a marker, stain and/or aromatizing agent

For preservation techniques by arterial insufflation (embalming) of human and mammal corpses and tissues for a relatively short period of time, for example 1 to 3 months, the compositions preferably have the following formulation:

15–20% dialkyl ($C_1$–$C_6$) ketone peroxide;

65–70% alcohol;

10–15% glycerol;

0–10% of a marker, stain and/or aromatizing agent

In preservation by immersion of animal and human corpses and tissues, the compositions preferably have the following formulation:

15–40% dialkyl ($C_1$–$C_6$) ketone peroxide;

10–15% glycerol;

50–70% alcohol;

0–5% of a marker, stain and/or aromatizing agent

For temporary preservation by application to the surface of animal and human corpses and tissues, the compositions preferably have the following formulation:

12–18% dialkyl ($C_1$–$C_6$) ketone peroxide;

10–30% glycerol;

47–78% alcohol;

0–10% of a marker, stain and/or aromatizing agent

For the preservation of bodies and tissues of reptiles and, in general, animals used for veterinary pathology and anatomy, the compositions preferably have the following formulation:

15–70% dialkyl ($C_1$–$C_6$) ketone peroxide;

10–15% glycerol;

15–70% alcohol;

0–10% of a marker, stain and/or aromatizing agent

For the preservation of marine animal bodies and tissues, the compositions preferably have the following formulation:

15–60% dialkyl ($C_1$–$C_6$) ketone peroxide;

10–15% glycerol;

15–65% alcohol;

0–10% of a marker, stain and/or aromatizing agent

For the preservation of bodies and tissues in entomology, the compositions preferably have the following formulation:

15–50% dialkyl ($C_1$–$C_6$) ketone peroxide;

10–15% glycerol;

30–70% alcohol;

0–10% of a marker, stain and/or aromatizing agent

The dialkyl ($C_1$–$C_6$) ketone peroxides ideal for the composition are conventional. As an example of a product on the market, the product (dialkyl ($C_1$–$C_6$) ketone peroxide) marketed by AKZO may be cited.

The most relevant function of the alcohol in the compositions is that of a vehicle that facilitates the mixing of the peroxide and the penetration and diffusion of the composition in the tissues. Ideal alcohols are, for example, conventional 60°, 70°, 80° and 96° alcohols and absolute ethanol.

Glycerol has the function of a wetting agent in the composition. Conventional glycerols, for example 10° and 30° glycerol are ideal.

The stains or aromatizing agents such as sarsaparilla are optional components that are mainly used as a stain of the muscle tissues, deodorization of the tissues that, prior to their preparation, have already begun to decay, etc.

The markers can be included to allow analysis of the manufacturing source of the composition. They must be inert, that is to say, they must not enter into reaction with the other components.

The full preserving and regenerating effects of the above mentioned compounds on the different tissues and preservation techniques, tend to be reached with exposure of the piece to the compositions according to the invention for 24 to 48 hours when long term or indefinite preservation effects are sought though, for certain applications, the duration of the exposure tends to be shorter when preservation for shorter periods of time is sought, such as preservation for the transport of corpses, storage of corpses in vaults before burial or identification thereof, etc.

After the preservatives have been applied according to the invention for only preserving purposes, their use in combination with suitable resins, in corrosion techniques with sodium hydroxide or potassium hydroxide for example, diaphanization of bodies or anatomical pieces, in staining of the central nervous system, in preservation techniques of cartilages and in microscopic capillary vascularization techniques.

Advantageously, the compositions of the present invention do not produce toxic residues or gases in the incineration of corpses or pieces prepared by means of the application of said compositions, nor do they produce dangerous polluting effluents in such corpses or pieces.

EMBODIMENTS OF THE INVENTION

The following examples, which are illustrative and representative but not limiting, describe practical embodiments of the invention.

EXAMPLE 1

A mixture that comprised per liter 600 ml/l of dialkyl ($C_1$–$C_6$) ketone peroxide 150 ml/l of glycerol 30°

200 ml/l of ethanol 96% v/v 50 ml/l of sarsaparilla was prepared by simple addition of the different components.

EXAMPLE 2

A mixture that comprised per liter 500 ml/l of dialkyl ($C_1$–$C_6$) ketone peroxide 100 ml/l of glycerol 30°

350 ml/l of ethanol 96% v/v 50 ml/l of sarsaparilla was prepared by simple addition of the different components.

EXAMPLE 3

A mixture of 400 ml/l of dialkyl ($C_1$–$C_6$) ketone peroxide 150 ml/l of glycerol 30°

400 ml/l of alcohol 80% v/v 50 ml/l of sarsaparilla was prepared by simple addition of the different components

EXAMPLE 4

A mixture of 350 ml of dialkyl ($C_1$–$C_6$) ketone peroxide 200 ml of glycerol 30°

400 ml of ethanol 70% v/v 50 ml of sarsaparilla was prepared by simple addition of the different components

EXAMPLE 5

A mixture of 300 ml of dialkyl ($C_1$–$C_6$) ketone peroxide 150 ml of glycerol 10°

600 ml of ethanol 60% v/v 50 ml of sarsaparilla was prepared by simple addition of the different components

EXAMPLE 6

A mixture of 150 ml of dialkyl ($C_1$–$C_6$) ketone peroxide 150 ml of glycerol 60% v/v 690 ml of ethanol 60% v/v 50 ml of chloral hyrate 50 ml of a conventional marker was prepared by simple addition of the different components

EXAMPLE 7

A human corpse was prepared by external washing with a conventional detergent substance, incision in the skin in the carotid and femoral regions to identify the arteries conventionally used for arterial insufflation of the preservatives. Conventional polyethylene catheters were introduced in these blood vessels and the composition described in example 1 in a proportion of about 80–100 cc. per kg. of weight of the corpse was injected by slow drip to facilitate the diffusion and impregnation thereof in the tissues.

The corpse prepared in this way was placed on a stainless steel tray with water. After having been subjected to variable temperatures between 0 and 30° C. after two years the corpse did not have any external signs of decay or contamination with fungi although the surrounding water as well as the tray were full of green, dark blue and mainly white fungi colonies.

All the joints of the body maintained their elasticity therefore the corpse could be placed in different positions by bending the different joints in a perfectly reversible manner without suffering any type of damage. Dissection of the corpse could be done with extraordinary ease and it showed that the anatomical structures of the corpse maintained their original structure and elasticity. Gentle non-progressive lipolysis possibly attributable to the action of the preservative could be observed.

EXAMPLE 8

Two anatomical pieces coming from a human corpse, in other words, a hemipelvis and a knee, were prepared by arterial insufflation with 80 to 100 cc per kg. of weight of the composition prepared according to example 1. The pieces were covered with polyethylene bags and buried in semi-humid soil at a depth of 30 cm. Three years later, the pieces were exhumed and inspected visually with regard to their outside appearance, by touch with regard to their mobility, and by means of dissection with regard to their anatomical characteristics.

The pieces were covered with fatty tissue though after cleaning them with water and a conventional detergent it was observed that they maintained their natural color;

they did not show any contamination with any fungi or any signs of decay, or destruction of their anatomical structures;

they maintained total elasticity and passive mobility.

Dissection of the pieces revealed that the knee and coxofemoral joints were preserved entirely and they kept the consistency and natural characteristics of their cartilages, capsule and ligamentous structures;

the blood vessels maintained enough elasticity and structural consistency to allow their insufflation.

EXAMPLE 9

Several lungs coming from human corpses were removed in different autopsies and immersed in the composition described in example 2 for 24 to 48 hours.

Subsequently, the composition described in example 2 was introduced by a conventional catheter and hypodermic syringe through the trachea. Very pressurized air was injected into the lungs by means of a conventional compressor and through the trachea, in order to obtain a uniform distribution of the preservative inside the lung.

6 to 12 hours later it was verified that upon insufflating and removing highly pressurized air through the trachea, the movements of pulmonary inspiration and expiration could be observed and that, therefore, the lung tissue retained its structure and elasticity intact.

EXAMPLE 10

Different pieces coming from human corpses, that is to say, a heart, a mesentery and a small intestine and the top part of an arm were prepared for insufflation of the blood vessels thereof with stains.

Said pieces were kept immersed in the composition described in example 2 for 24 to 48 hours. Subsequently, the composition prepared according to example 1 in a proportional amount to each piece was injected by means of a hypodermic syringe with a caliber suitable to the dimensions of the blood vessel.

Then, the pieces were kept immersed in the composition prepared according to example 2 for 24 hours after which the pieces were removed and air was introduced in the blood vessels in order to clean them. Then, a stain comprised of gelatin was injected in the vessels.

It was possible to observe in all the pieces that the stain was introduced up to the fine capillaries, a total absence of blood clots as well as a great elasticity of all the vessels. Upon injecting air, it was possible to simulate vascular dilatation.

EXAMPLE 11

A dog's head was kept immersed in a composition prepared according to example 3 for 24 hours. Afterwards, a composition prepared according to example 3 was injected in the main arteries by techniques and in an amount equivalent to the application of conventional embalming with formaldehyde.

After 36 hours it was possible to observe total regeneration of the passive mobility of the jaw, tongue, eyelids, exceptional whitening of the teeth as well as total flexibility of all the tissues of the head. After two years, the head, exposed to room temperature, did not have any sign of loss of the above cited qualities, nor any decay or microbiological or fungal contamination.

EXAMPLE 12

Three common lizards were kept immersed in a composition prepared according to example 3 for 48 hours.

It was possible to verify that, after immersion, the animals maintained total elasticity of the skin and joints as well as a totally natural appearance. These qualities remained present 6 months after immersion. Besides, the animals did not have any sign of decay, fungal or microbiological contamination or mummification.

EXAMPLE 13

Ten fish of the golden carp species were kept submerged in a composition prepared according to example 4 for 24 hours. It was possible to verify that, after immersion, the animals maintained total elasticity in the fins, skin and joints as well as a totally natural appearance. These qualities remained present 6 months after immersion. Besides, the animals did not have any sign of decay, fungal or microbiological contamination or mummification.

EXAMPLE 14

Fifty common bees were kept submerged in a composition prepared according to example 5 for 24 hours. It was possible to verify that, after immersion, the animals maintained total elasticity in the wings, skin and joints as well as a totally natural aspect. These qualities remained present 6 months after immersion. Besides, the animals did not have any sign of decay, fungal or microbiological contamination or mummification.

EXAMPLE 15

A human corpse was placed, 6 hours after death, on a smooth and waterproof surface. Preferably (though not indispensably) the natural orifices were plugged up gently with cotton impregnated with a composition prepared according to any of the examples 1, 2 or 6.

With a brush from 6 to 10 cm. wide, or by a conventional sprayer with mechanical-manual pressure, the composition prepared in accordance with example 6 was applied to the entire surface of the corpse until the corpse was uniformly impregnated.

When the corpse in question is heavy, edematized or has signs of decay or fermentation, above all at the abdominal level, free injection of 100 cc of the composition prepared according to example 6 in the thoracic and abdominal cavities is advisable.

When the corpses in question are mutilated, the mutilated areas may be additionally injected with 20 to 25 cc in order to improve the preservation of such areas.

Due to the slightly oily nature of the preservative, it is advisable to let the corpse rest for 60 to 90 minutes without any clothing.

The corpses prepared in this manner can be kept at room temperature for 3 to 20 days, which is especially advantageous for example for those corpses that need to be transported short or medium distances, or that have to remain in funeral parlors.

If bad odors or signs of decay are observed, application of the composition on the surface of the corpse as described before may be repeated, for example, three and/or seven days after the first treatment.

EXAMPLE 16

For whitening thereof, the bony piece, once the soft matter that it may be partially or totally covered with has been removed, is introduced in a composition prepared according to example 2 for a period of one to three weeks, depending on the size thereof.

Then, the piece is drained off and placed in an alcohol 96% bath for 3 to 7 days.

Afterwards, the piece is removed from the alcohol bath and is kept at room temperature until it has completely dried (for about 1 to 2 days.)

It can be observed that even when the pieces in question come from burials, the treatment described above produces total whitening.

EXAMPLE 17

A mummified corpse is subjected to restoration for which purpose its surface is cleaned first of all, the inorganic remains come off and then it is submerged in a bath with a composition prepared according to example 2 for a minimum period of 3 to 5 days.

During this period, it can be observed that the mummified corpse begins to progressively become clarified at the same time that its tissues and even its joints acquire flexibility. Once the color and elasticity sought have been observed, the corpse is removed from the bath and, once it has been drained off, it can be exposed at room temperature for practically an indefinite period of time.

In the event that later on some exsiccation takes place, it may be overcome by introducing the corpse in the bath described above for 2 to 3 days.

EXAMPLE 18

One part of nervous tissue is fixed and sectioned and submerged for about 15 minutes in a solution of 5 g of copper sulfate in 500 ml of distilled water. The tissue is removed and washed in abundant distilled water for 1 to 2 minutes.

After washing, the tissue is submerged in a solution of 5 g of potassium ferrocyanate in 500 ml. of distilled water. The tissue is removed and washed in abundant distilled water for 5 to 15 seconds.

After the second washing, the piece is submerged in ferric chloride for about 15 seconds, then it is washed again in abundant distilled water for 5 to 10 minutes. When a very light tone is desired in the preserved tissue, the tissue is additionally submerged in a copper sulfate solution for a few minutes.

The washed tissue is submerged in alcohol 96° for 5 to 6 minutes and then it is submerged for 15 to 30 minutes in a solution prepared according to example 2, until the tissue has acquired a light brown tone.

The nervous tissue treated in this way remains flexible and does not decay when it is exposed to room temperature.

EXAMPLE 19

In order to flexibilize hollow viscera, such as lungs, intestines, etc. for example, the pieces (previously emptied) are introduced in a solution prepared according to example 2 for 24 to 72 hours. During this time and being completely immersed, the pieces are also insufflated at a very low pressure with said solution, in the event of pulmonary blocking through the trachea and in the case of intestinal mass through one of its ends, by linking the other end. In this way, not only is cleaning of the contents achieved but also the total elasticity and preservation of the viscera. Elasticity of the pieces treated in this way is practically the same as that of live tissues.

Once the pieces have been removed from the solution, they may be insufflated with low pressurized air, or filled with synthetic resins, stained elastic latex or semisolid stains. Preferably, the pieces are stored in polyethylene bags and are wrapped in cloths or cotton slightly impregnated with the composition according to example 1 or 2.

EXAMPLE 20

In order to obtain samples of blood vessels, a corrosion-reflection technique that is described using a kidney as an example, is used.

Through a catheter, a solution according to example 2 is injected in the renal artery until all the arterial vessels are full of said solution.

The piece treated in this way is placed on a non-porous surface at room temperature for 24 to 48 hours. After resting, conventional acrylic resin is introduced in the arterial vessels, though the renal artery, until the piece has acquired the desired consistency.

Then the piece is submerged in an aqueous solution that contains from 15 to 20 g. of sodium hydroxide per liter of water, until all the kidney tissue has been corroded and the resin mold of the arterial vessels, including that of the finest capillaries, remains exposed.

The piece is cleaned with water and may be exposed to room temperature without any type of protection.

EXAMPLE 21

The following procedure is used for diaphanization techniques (of fetuses for example).

The piece is completely immersed in a solution according to example 2 for a minimum of 48 hours and a maximum of 7 days, depending on the type of piece in question. Then the piece is drained off and is kept in a solution of 2 g. of alizarin per liter of alcohol 50° for 3 to 5 hours, and is submerged in a solution according to example 2 for about 5 to 7 days, until the same is completely diaphanized. The diaphanized piece may be exposed at room temperature without any type of protection or coating, which advantageously stands out over the pieces diaphanized by conventional methods that require them to be kept in glycerol. Another advantage of the use of the compositions of the present invention is that diaphanization substantially requires less time than diaphanization carried out with formol/formaldehyde that usually requires about 120 days.

In those cases in which the pieces remain exposed for prolonged periods in hot environments, diaphanization may be reduced. To recover the complete diaphanization in these cases it suffices to submerge the pieces again in a solution according to example 2.

We claim:

1. A composition for preserving organic animal or human tissues, containing a basis formulation that comprises, by volume %

12 to 70% of dialkyl ($C_1$–$C_6$) ketone peroxide;

10 to 15% of glycerol;

15 to 75% of alcohol;

0 to 10% of at least one additive selected from the group consisting of markers, dyes, fragrancing agents and mixtures thereof.

2. A composition according to claim 1, wherein the formulation comprises 50 to 70% of dialkyl ($C_1$–$C_6$) ketone peroxide;

10–15% of glycerol;

15–30% alcohol;

0–5% of additive.

3. A composition according to claim 1, wherein the formulation comprises

15–20% of dialkyl ($C_1$–$C_6$) ketone peroxide;

10–15% of glycerol;

65–70% of alcohol;

0–10% of additive.

4. A composition according to claim 1, wherein the formulation comprises

15–40% of dialkyl ($C_1$–$C_6$) ketone peroxide;

10–15% of glycerol;

50–70% of alcohol;

0–10% of additive.

5. A composition according to claim 1, wherein the formulation comprises

15–70% of dialkyl ($C_1$–$C_6$) ketone peroxide;

10–15% of glycerol;

15–70% of alcohol;

0–5% of additive.

6. A composition according to claim 1, wherein the formulation comprises

15–60% of dialkyl ($C_1$–$C_6$) ketone peroxide;

10–15% of glycerol;

15–65% of alcohol;

0–10% of additive.

7. A composition according to claim 1, wherein the formulation comprises

15–50% of dialkyl ($C_1$–$C_6$) ketone peroxide;

10–15% of glycerol;

30–70% of alcohol;

0–10% of additive.

8. A composition according to claim 1, wherein the formulation comprises
   12–18% of dialkyl ($C_1$–$C_6$) ketone peroxide;
   10–30% of glycerol;
   47–78% of alcohol;
   0–10% of additive.

9. A composition according to claim 1, wherein the formulation comprises per liter
   600 ml/l of dialkyl ($C_1$–$C_6$) ketone peroxide;
   150 ml/l of glycerol;
   200 ml/l of alcohol;
   50 ml/l of additive.

10. A composition according to claim 1, wherein the formulation comprises per liter
   500 ml/l of dialkyl ($C_1$–$C_6$) ketone peroxide;
   100 ml/l of glycerol;
   350 ml/l of alcohol;
   50 ml/l of additive.

11. A composition according to claim 1, wherein the formulation comprises per liter
   400 ml of dialkyl ($C_1$–$C_6$) ketone peroxide;
   150 ml of glycerol;
   400 ml of alcohol;
   50 ml of additive.

12. A composition according to claim 1, wherein the formulation comprises per liter
   350 ml of dialkyl ($C_1$–$C_6$) ketone peroxide;
   200 ml of glycerol;
   400 ml of alcohol;
   50 ml. of additive.

13. A composition according to claim 1, wherein the formulation comprises per liter
   300 ml of dialkyl ($C_1$–$C_6$) ketone peroxide;
   150 ml of glycerol;
   600 ml of alcohol;
   50 ml of additive.

14. A composition according to claim 1, wherein the formulation comprises per liter
   150 ml of dialkyl ($C_1$–$C_6$) ketone peroxide;
   150 ml of glycerol 10%;
   690 ml of ethanol 60% v/v;
   50 ml of chloral hydrate as a dye;
   50 ml of a marker.

15. A composition according to claim 1, wherein dialkyl ($C_1$–$C_6$) ketone peroxide selected from the group consisting of ethyl-methyl ketone peroxide, methyl isobutyl ketone peroxide, and mixtures thereof.

16. A composition according to claim 1, wherein glycerol is selected from the group consisting of glycerol of 30%, glycerol of 10% and mixtures thereof.

17. A composition according to claim 1, wherein alcohol is selected from the group consisting of ethanol, absolute ethanol, alcohol of 96%, alcohol of 80%, alcohol of 70%, alcohol of 60% and mixtures thereof.

18. A composition according to claim 1, wherein the dye is selected from chloral hydrate and sarsaparilla.

19. A composition according to claim 1, wherein the fragrancing agent is citronella.

20. A method of treating dead human and animal tissue for preservation, anatomical preparation and/or regeneration of dead human and animal tissue the method comprising applying to the tissue, by a technique selected from immersion, spraying, daubing, embalming and combinations thereof, an effective amount of a composition containing a formulation that comprises in volume %
   12 to 70% of dialkyl ($C_1$–$C_6$) ketone peroxide;
   10 to 15% of glycerol;
   15 to 75% of alcohol;
   0 to 10% of at least one additive selected from the group consisting of markers, dyes, fragrancing agents and mixtures thereof thereby heating the tissue for preservation anatomical preparation and/or regeneration of tissues.

21. A method according to claim 20, wherein a human or mammal corpse or tissue is embalmed by applying an effective amount of a composition containing a formulation that comprises
   50–70% of dialkyl ($C_1$–$C_6$) ketone peroxide;
   10–15% of glycerol;
   15–30% of alcohol;
   0–5% of additive for preservation for at least two years.

22. A method according to claim 20, wherein a human or mammal corpse or tissue is embalmed by applying an effective amount of a composition containing a formulation that comprises
   15–20% of dialkyl ($C_1$–$C_6$) ketone peroxide;
   10–15% of glycerol;
   65–70% of alcohol;
   0–10% additive for preservation for a period of time shorter than six months.

23. A method according to claim 20, wherein a human or animal corpse or tissue is immersed for preservation in a composition containing a formulation that comprises
   15–40% of dialkyl ($C_1$–$C_6$) ketone peroxide;
   10–15% of glycerol;
   50–70% of alcohol;
   0–10% of additive.

24. A method according to claim 20, wherein a mammal or reptile corpse is treated with an effective amount of a composition containing a formulation that comprises
   15–70% of dialkyl ($C_1$–$C_6$) ketone peroxide;
   10–15% of glycerol;
   15–70% of alcohol;
   0–5% of additive for preservation and anatomical preparation.

25. A method according to claim 20, wherein a dead marine animal or tissue thereof is treated with an effective amount of a composition containing a formulation that comprises
   15–60% of dialkyl ($C_1$–$C_6$) ketone peroxide;
   10–15% of glycerol;
   15–65% of alcohol;
   0–10% of additive for preservation and anatomical preparation.

26. A method according to claim 20, wherein a dead insect is treated with an effective amount of a composition containing a formulation that comprises
   15–50% of dialkyl ($C_1$–$C_6$) ketone peroxide;
   10–15% of glycerol;
   30–70% of alcohol;
   0–10% of additive for preservation and preparation in entomology.

27. A method according to claim 20, wherein a human or mammal corpse or tissue is embalmed by applying an effective amount of a composition containing a formulation that comprises, per liter
- 600 ml/l of dialkyl ($C_1$–$C_6$) ketone peroxide;
- 150 ml/l of glycerol;
- 200 ml/l of alcohol;
- 50 ml/l of additive for preservation for at least two years.

28. A method according to claim 20 wherein a human or mammal corpse or tissue is embalmed by applying an effective amount of a composition containing a formulation that comprises, per liter
- 500 ml/l of dialkyl ($C_1$–$C_6$) ketone peroxide;
- 100 ml/l of glycerol;
- 350 ml/l of alcohol;
- 50 ml/l of additive for preservation for at least two years.

29. A method according to claim 20, wherein the composition contains a formulation that comprises, per liter
- 400 ml of dialkyl ($C_1$–$C_6$) ketone peroxide;
- 150 ml of glycerol;
- 400 ml of alcohol;
- 50 ml of additive.

30. A method according to claim 20, wherein the composition contains formulation that comprises, per liter
- 350 ml of dialkyl ($C_1$–$C_6$) ketone peroxide;
- 200 ml of glycerol;
- 400 ml of alcohol;
- 50 ml of additive.

31. A method according to claim 20, wherein a dead insect or a tissue thereof is treated with an effective amount of a composition containing a formulation that comprises, per liter
- 300 ml of dialkyl ($C_1$–$C_6$) ketone peroxide;
- 150 ml of glycerol;
- 600 ml of alcohol;
- 50 ml of additive for preparation and/or preservation in entomology thereof.

32. A method according to claim 20, wherein a human or animal corpse is daubed with an effective amount of a composition containing a formulation that comprises, per liter
- 150 ml of dialkyl ($C_1$–$C_6$) ketone peroxide;
- 150 ml of glycerol 10%;
- 690 ml of ethanol 60% v/v;
- 50 ml of chloral hydrate;
- 50 ml of a marker for temporary preservation thereof.

33. A method according to claim 20, for wherein dead human or animal tissue is treated with an effective amount of the composition for regenerating flexibility thereof.

34. A method according to claim 20, wherein an effective amount of a composition containing a formulation that comprises, per liter
- 150 ml of dialkyl ($C_1$–$C_6$) ketone peroxide;
- 150 ml of glycerol 10%;
- 690 ml of ethanol 60% v/v;
- 50 ml of chloral hydrate;
- 50 ml of a conventional marker is sprayed on the surface of a human or animal corpse for temporary preservation thereof.

35. A method according to claim 20, wherein dialkyl ($C_1$–$C_6$) ketone peroxide selected from the group consisting of ethyl-methyl ketone peroxide, methyl isobutyl ketone peroxide, and mixtures thereof.

36. A method according to claim 20, wherein glycerol is selected from the group consisting of glycerol of 30%, glycerol of 10% and mixtures thereof.

37. A method according to claim 20, wherein alcohol is selected from the group consisting of ethanol, absolute ethanol, alcohol of 96%, alcohol of 80%, alcohol of 70%, alcohol of 60% and mixtures thereof.

38. A method according to claim 20, wherein the dye is selected from chloral hydrate and sarsaparilla.

39. A method according to claim 20, wherein the fragrancing agent is citronella.

* * * * *